(12) United States Patent
Stelmar Netto et al.

(10) Patent No.: US 11,663,923 B2
(45) Date of Patent: May 30, 2023

(54) SCREENING MATERIAL WASTE

(71) Applicant: International Business Machines Corporation, Armonk, NY (US)

(72) Inventors: Marco Aurelio Stelmar Netto, Sao Paulo (BR); Carlos Henrique Cardonha, Sao Paulo (BR); Igor Cerqueira Oliveira, Sao Paulo (BR)

(73) Assignee: International Business Machines Corporation, Armonk, NY (US)

( * ) Notice: Subject to any disclaimer, the term of this patent is extended or adjusted under 35 U.S.C. 154(b) by 1217 days.

(21) Appl. No.: 16/205,671

(22) Filed: Nov. 30, 2018

(65) Prior Publication Data
US 2020/0175883 A1 Jun. 4, 2020

(51) Int. Cl.
*G09B 19/00* (2006.01)
*G09B 5/00* (2006.01)
*G06Q 10/30* (2023.01)
*G01N 33/02* (2006.01)
*G01N 5/00* (2006.01)
*G01N 29/14* (2006.01)

(52) U.S. Cl.
CPC ............... *G09B 5/00* (2013.01); *G01N 5/00* (2013.01); *G01N 29/14* (2013.01); *G01N 33/02* (2013.01); *G06Q 10/30* (2013.01); *G09B 19/00* (2013.01)

(58) Field of Classification Search
CPC . G09B 5/00; G09B 19/00; G01N 5/00; G01N 29/14; G01N 33/02; G01N 29/4445; G01N 2291/02458; G06Q 10/30; Y02W 90/00
See application file for complete search history.

(56) References Cited

U.S. PATENT DOCUMENTS

| | | | |
|---|---|---|---|
| 9,352,887 B2 * | 5/2016 | Poss | B65F 1/1426 |
| 9,573,167 B2 * | 2/2017 | Marrapodi | B07C 5/3412 |
| 9,888,159 B2 | 2/2018 | Loh | |
| 10,888,901 B2 * | 1/2021 | Ward | B07C 5/02 |
| 10,898,927 B2 * | 1/2021 | Ripley | B07C 5/342 |
| 11,104,512 B2 * | 8/2021 | Krishnamurthy | B65F 1/1426 |
| 11,273,977 B2 * | 3/2022 | Giaever | B65F 1/0033 |
| 2004/0133484 A1 * | 7/2004 | Kreiner | B07C 5/3412 |
| | | | 705/28 |
| 2004/0199401 A1 * | 10/2004 | Wagner | G06Q 10/06 |
| | | | 705/308 |
| 2010/0185506 A1 | 7/2010 | Wolff et al. | |
| 2014/0214505 A1 * | 7/2014 | Shuster-Arechiga | |
| | | | G06Q 30/0208 |
| | | | 705/308 |
| 2014/0305851 A1 * | 10/2014 | Hubbell | B65F 1/1473 |
| | | | 209/552 |

(Continued)

OTHER PUBLICATIONS

NPL , Smart Recyle Bin , Published Sep. 12, 2017 (Year: 2017).*

(Continued)

*Primary Examiner* — Masud Ahmed
(74) *Attorney, Agent, or Firm* — Cantor Colburn LLP; Michael Petrocelli

(57) ABSTRACT

Material waste screening is provided. A sensor obtains data related to an object. A processor classifies the object based on the data to identify a recycle category for the object, open a recycle bin for the identified recycle category, instruct the operator to deposit the object in the opened recycle bin, determine a level of compliance of the object, and create at least one new instruction to increase the level of compliance.

14 Claims, 4 Drawing Sheets

(56) References Cited

U.S. PATENT DOCUMENTS

2018/0016096 A1* 1/2018 Krishnamurthy ......... B65F 1/14

OTHER PUBLICATIONS

Heng, Franklin, et al., "VisionCycle," https://www.edwardqiu.com/pdfs/visioncycle.pdf (retrieved Nov. 30, 2018), 12 pages.
Ling, Cong, et al., "SortBot: Self-sorting Recycling Machine," Mar. 13, 2017, Imperial College, London, 32 pages.
Torres-Garcia, Andres, et al., "Intelligent Waste Separator," Computación y Sistemas, vol. 19, No. 3, 2015, pp. 487-500.
Yang, Mindy, et al., "Classification of Trash for Recyclability Status," CS229 Project Report, 2016, 6 pages.

* cited by examiner

SCREENING MATERIAL WASTE

BACKGROUND

The present invention relates to computing devices, and more specifically, to a computer systems and computer-implemented methods for screening material waste through a disposal or recycling process.

Recycling has become a common practice. Computers and computer device can be used to recognize and separate recyclable materials from each other and from non-recyclable trash. However most recycling, for the consumer, still involves having people toss articles made from different materials into different assigned bins. People who are careless or who are unsupervised in their recycling process can place items of one material into a bin meant for other materials. A computer-based advisor is needed at garbage collection stations in order to supervise a recycler through the recycling process.

SUMMARY

Embodiments of the present invention are directed to a computer-implemented method of executing an interactive advisor. A non-limiting example of the computer-implemented method includes: sensing an object to be recycled using a sensor; classifying, at a processor, the sensed object to identify a recycle category for the object; opening, by the processor, a recycle bin suitable for the recycle category; instructing, by the processor, an operator to deposit the object in the opened recycle bin; determining, at the processor, a level of compliance of the object with instructions; and creating, at the processor, at least one new instruction to increase the level of compliance.

Embodiments of the present invention are directed to an interactive advisor. A non-limiting example of the interactive advisor includes: a sensor configured to obtained data related to an object; and a processor configured to: classify the object based on the data to identify a recycle category for the object; open a recycle bin for the identified recycle category; instruct the operator to deposit the object in the opened recycle bin; determine a level of compliance of the object with instructions; and create at least one new instruction to increase the level of compliance.

Embodiments of the present invention are directed to computer program product for operating a garbage collection station. A non-limiting example of the computer program product includes: a computer readable storage medium having program instructions embodied therewith, the program instructions executable by a processor to cause the processor to perform operations including: sensing an object to be recycled using a sensor; classifying the sensed object to identify a recycle category for the object; opening a recycle bin suitable for the recycle category; instructing an operator to deposit the object in the opened recycle bin; determining a level of compliance of the object with instructions; and creating at least one new instruction to increase the level of compliance.

DETAILED DESCRIPTION

Embodiments of the invention disclosed herein disclose computer-implemented methods and computer systems configured and arranged to assist with the process of recycling an item. An example method includes a sensing an object to be recycled using a sensor. An interactive advisor is used to determine a recycle category for the object. The advisory then opens a recycle bin suitable for the recycle category and instructs an operator to deposit the object in the opened recycle bin. The interactive advisory can provide instructions to the operator in order to properly dispose of the item. In addition, the interactive advisory can determine the degree of compliance of an object with the instructions and alter the instructions as considered necessary in order to increase the operator's object or the compliance of other objects in the future. The interactive advisory can evaluate the compliance of the object using a machine learning program. The machine learning program can also formulate a new procedure or a new step in an existing procedure in order to increase compliance and observe the effect of the procedure or new step in increasing the compliance.

Machine Learning gives computers the ability to "learn" without being explicitly programmed Machine learning explores the study and construction of algorithms that can learn from and make predictions on data. Such algorithms overcome following strictly static program instructions by making data-driven predictions or decisions, through building a model from sample inputs. Machine Learning can be supervised, unsupervised or reinforced. In supervised learning, a computer is presented with example inputs and their desired outputs, given by a "teacher," with the goal of learning a general rule that maps inputs to outputs. In unsupervised learning, no labels are given to the learning algorithm, leaving it on its own to find structure in its input. Unsupervised learning can be a goal in itself (such as discovering hidden patterns in data) or a means towards an end (such as feature learning). In reinforcement learning, a computer program interacts with a dynamic environment in which it must perform a certain goal (such as driving a vehicle or playing a game against an opponent). The program is provided feedback in terms of rewards and punishments as it navigates its problem space.

Figure 1:
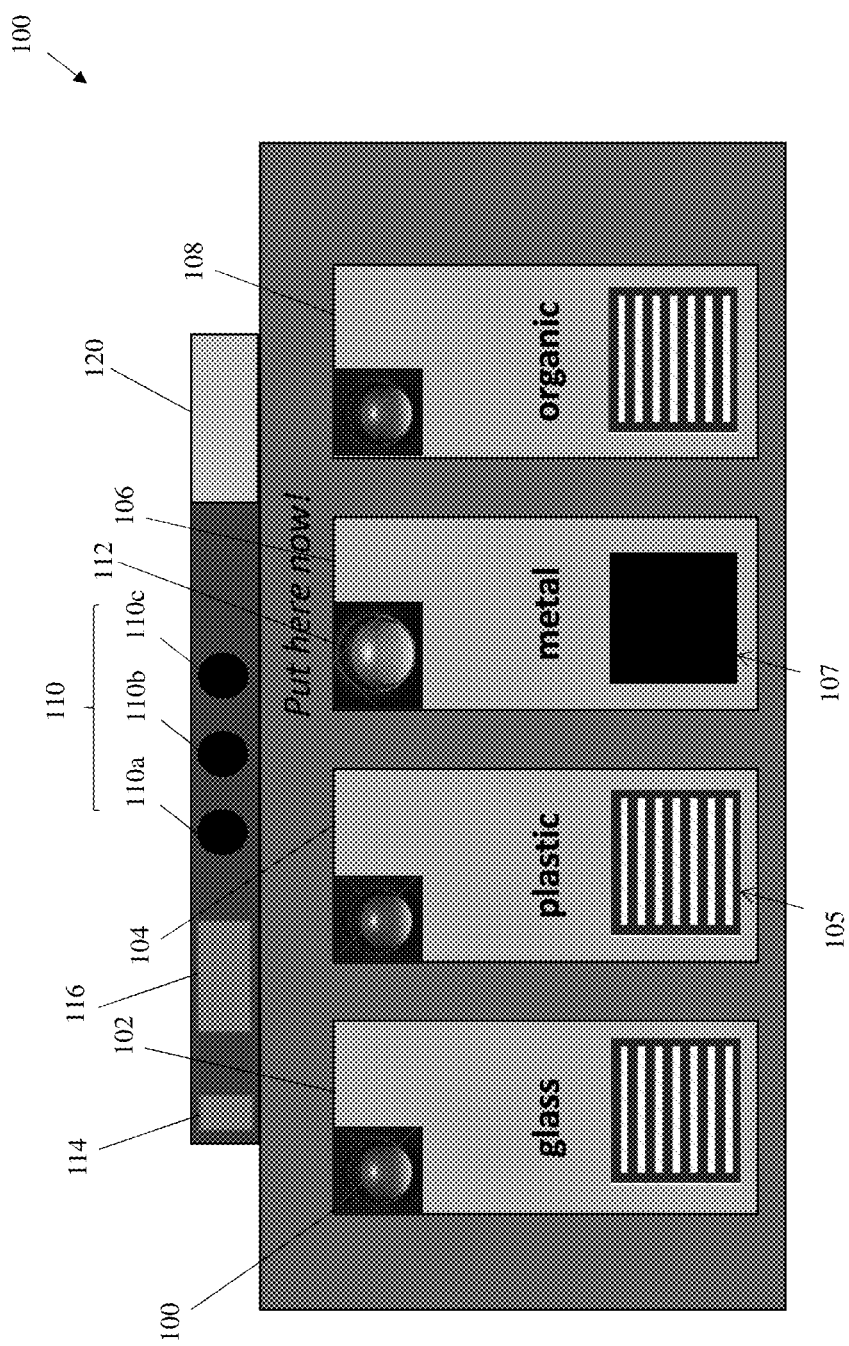
FIG. 1 depicts a garbage collection station that employs an interactive advisor to aid people in the proper recycling of their recyclable items or objects according to embodiments of the invention.

Turning now to FIG. 1, FIG. 1 depicts a garbage collection station 100 or recycling bin that employs an interactive advisor to aid people in the proper recycling of their recyclable items or objects. The station 100 includes a plurality of bins 102, 104, 106 and 108 for receiving recyclable objects. Each bin has a door, cover, hatch or lid 105 that can be opened and closed in order to allow certain recyclable material to be entered therein. Each bin is further assigned to accept items within a defined recycle category. For example, bin 102 accepts glass, bin 104 accepts plastics, bin 106 accepts metal and bin 108 accepts organic material. It is understood that these particular categories are provided for illustrative purposes only and that any number for bins and any suitable recycle category can be provided in different embodiments of the garbage collection station 100. An operator is a person that uses the garbage collection station 100 in order to deposit a recyclable item. As discussed herein, the recycling process includes the actions or steps taken by the operator, often under instruction by the garbage collection station 100, in disposing of an item at the garbage collection station.

The garbage collection station 100 further includes various data sensors 110 that are used to identify items that have been brought to the garbage collection station 100 for recycling. In one embodiment the data sensors includes a visual sensor 110a such as a digital camera that captures an image of the object. In addition, the data sensors 110 can include an audio sensor 110b that captures a sound of the object and a smell sensor 110c that captures a smell of the object.

The garbage collection station 100 further includes an interactive advisor or a control unit 120 that controls operation of the garbage collection station 100. The control unit 120 receives data from the data sensors 110 in order to determine a recycle category for the item, and controls operation of the garbage collection station 100 accordingly. The control unit 120 can communicate with an operator in order to guide the operator through the recycling process. Thus, the control unit 120 communicates with the operator via lights 112, speaker 114, display 116, etc. The control unit 120 can also open a bin that corresponds to a material of an item sensed by the sensors 110 and can provide an indication to the operator of which bin should be used.

As an illustrative example, the operator approaches the garbage collection station 100 with an item. The garbage collection station 100 obtains an image of the item using visual sensor 110a and determines that the item is a metal item. The garbage collection station 100 then opens the lid 105 for the "metal" bin 106 and to reveal an opening 107 and changes a color of a light 112 associated with the bin 106 to a color indicating that the bin is open for the item. For this example, the light 112 is changed from a red color to a green color when the lid 105 is opened. When the item has been deposited into the bin 106, the garbage collection station 100 closes the bin 106 and changes the light 112 back to a color indicating that bin is closed (e.g., the color red).

Figure 2:
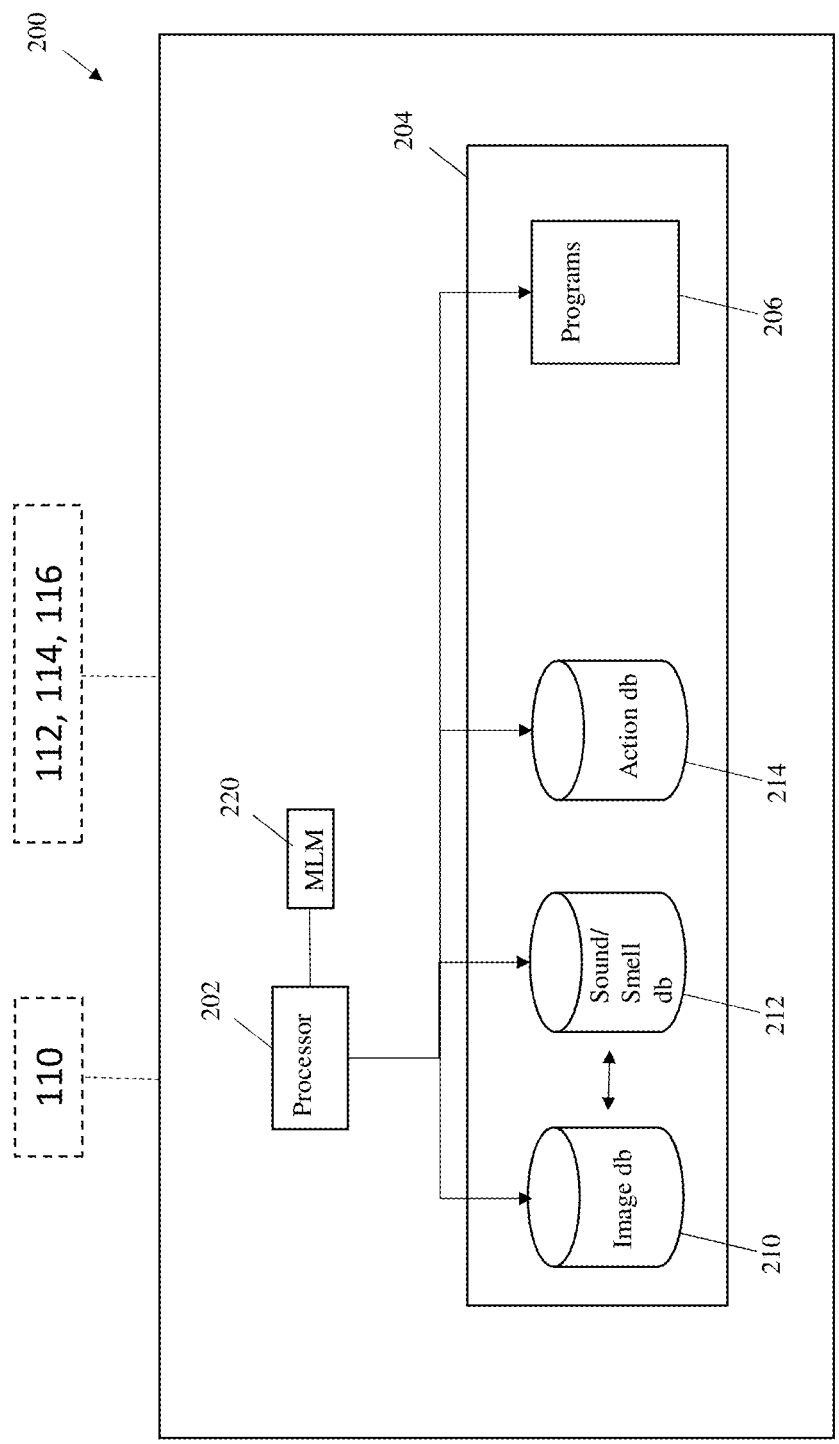
FIG. 2 depicts a schematic diagram illustrating the components of a control unit of the garbage collection station of FIG. 1.

FIG. 2 depicts a schematic diagram illustrating the components of the control unit 120. The control unit 120 includes a processor 202 and a memory storage device 204 accessible to the processor 202. The memory storage device 204 stores therein programs 206 that when accessed by the processor 202, enable the processor 202 to control an operation of the garbage collection station 100 by performing the various methods discussed herein. Additionally, the memory storage device 202 stores various databases 210, 212 and 214 that are used to identify an object that is being brought to the garbage collection station 100 and to provide instructions for the operator to follow in order to properly dispose of the item. The processor 202 can operate or be in communication with a machine-learning module 220 that performs various learning and compliance testing operations.

In various embodiments, the memory storage device 204 includes an image database 210. The processor 202 receives an image of the object from the sensors 110 and compares the image to a stored image in the image database 210 in order to determine a recycle category for the item. The processor 202 determines what type of item is in the image and thereby determines the recycle category. The processor 202 can further determine from the image that the item includes multiple components, each of a different recycle category. The memory storage device 204 further includes a sound/smell database 212. The processor 202 accesses the sound/smell database 212 to further determine the type of recycle category.

In various embodiments, the act of determining a recycle category for an item includes a coarse-grained identification of the item and a fine-grained identification of the item. In various embodiments, the coarse-grained identification includes identifying the recycle category for a simple recyclable item or an item made of a single recyclable material. The fine-grained identification can be used to identify additional characteristics of the item that is not identified in the coarse-grained step. For example, the item can include components from two different recycle categories and require separation of the item into its components. In addition, the fine-grained identification can identify not just a recycle category for the item but also a recyclable state of the item. The recyclable state refers to a readiness of the item to be accepted at the garbage collection station. For example, if the item needs to be separated into its components (e.g., a plastic component and a paper component), then the item is not ready to be accepted at the garbage collection station. In another example, if there is still food left in a container (e.g., a bag of chips with some chips remaining or a plastic bottle of soda with some soda remaining), then the item is not ready to be accepted at the garbage collection station 100. Depending on the recyclable state of the item, the control unit 120 can provide a suitable set of instructions for properly guiding the operator through the recycling process. Fine-grained characteristics can include a vector of features. Vectors may consist of Boolean variables, each indicating whether content of a certain type is present or not (e.g., if bag of chips has residues, if a beverage can has a significant amount of liquid, etc.)

In various embodiments, the sound/smell database 212 can be used to determine the fine-grained identification of the item. For example, by shaking a bag of chips, the resulting sound can be used to identify that some chips are still in the bag, requiring that the bag be emptied out prior to depositing into a recycle bin. Smell sensors can be used to determine food remaining in a container, requiring the container to be emptied out prior to depositing into the recycle bin.

Action database 214 includes one or more actions that are to be taken in order to recycle an item based on the recyclable state. The processor 202 compares a recycle category determined using the image database 210 and sound/smell database 212 in order to determine an action for the operator to take in order to properly deposit the recyclable item. The processor 202 then provides the actions to the user to allow the user to properly dispose of the recyclable item. The actions from the action database 214 can be extracted based on the vector of fine-grained characteristics. When an exact match of vector to action is available, the processor 202 can retrieve a most similar action and notify the operator that the instructions are approximate.

Figure 3:
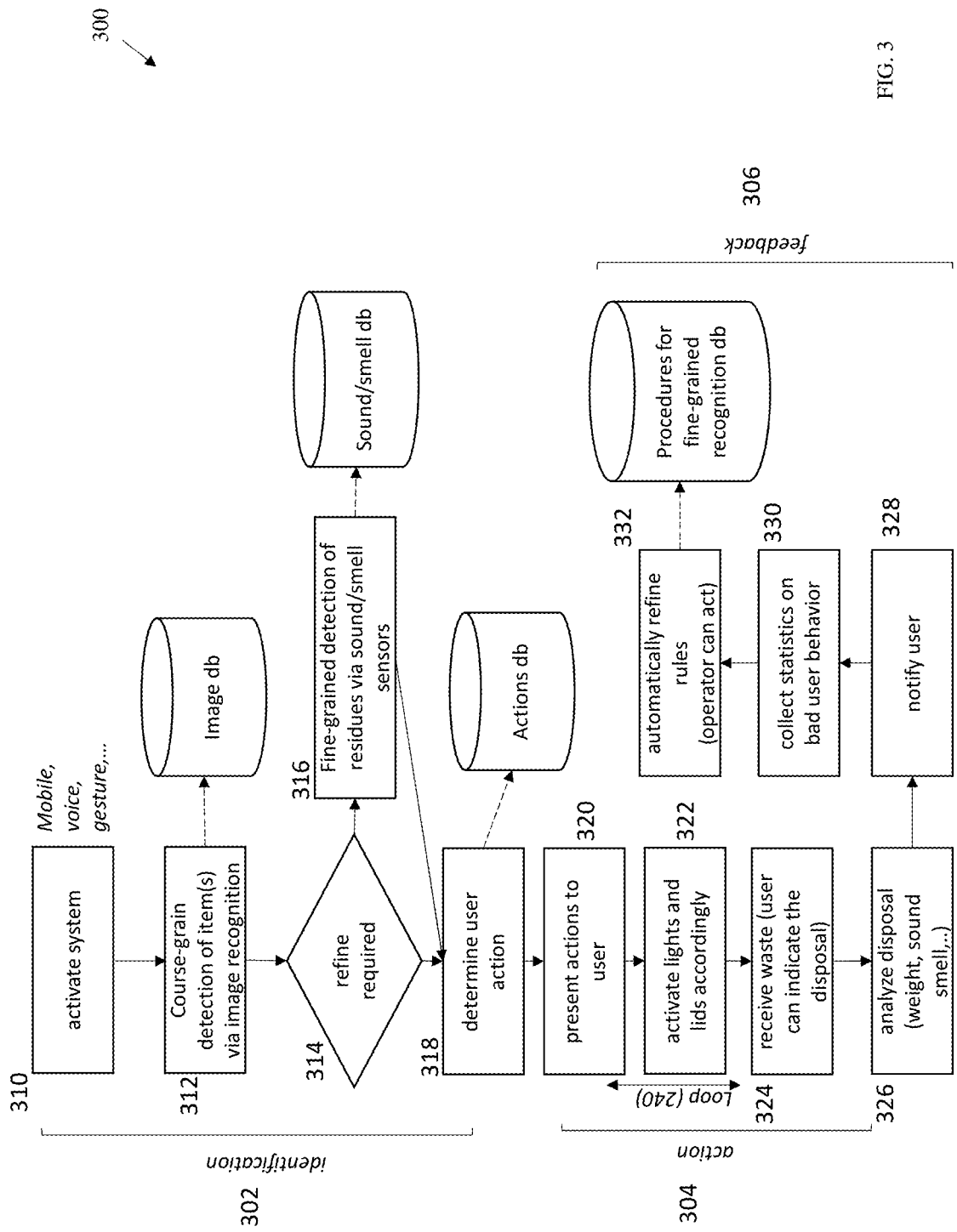
FIG. 3 shows a flowchart illustrating a computer-implemented method of operation of the garbage collection station of FIG. 1.

FIG. 3 shows a flowchart 300 illustrating a method of operation of the garbage collection station 100 of FIG. 1 in an exemplary embodiment. The flowchart 300 includes an identification stage 302, an action stage 304 and a feedback stage 306. The identification stage 302 includes the coarse-grained and fine-grained determination of the item. During the action stage 304, the control unit 120 communicates with the operator in order to provide instructions for the operator to follow in order to properly recycle the item. In the feedback stage 306, the control unit 120 evaluates the compliance of the object with the instructions provided during the action stage 304 and refines action rules for the operator to follow in order to increase compliance of an object for future operations. In various embodiments, a machine learning module can evaluate the compliance of the object and create the action rules for increasing compliance based on the compliance of the object. The machine learning module can also observe and evaluate the effect of the new procedure or new step in increasing the compliance as intended.

The flow chart 300 begins at box 310 in which the garbage collection station 100, FIG. 1 is activated by an appropriate activation signal such as a voice signal, a gesture, a signal sent from a mobile device etc. In box 312, coarse-grained identification of the item is performed by image recognition of a captured image of the item. In various embodiments, the operator holds the item in front of the image sensor 110*a* to allow the image sensor 110*a* to capture an image of the item. By comparing the image with a stored image in the image database 210, the processor 202 is able to identify the item.

At decision box 314, the processor 202 determines whether a more fine-grained identification of the item is necessary. If yes, the flowchart proceeds to box 316. In box 308, a sound or smell of the item is obtained by audio sensor 110*b* and/or smell sensor 110*c*. The sounds and/or smells associated with the item compared to recorded sounds and/or smells in the sound/smell database 212 in order to determine a fine-grained identification of the item. For example, upon receiving instructions from the control unit 120, the operator can make a sound with the item or place the item near a smell sensor. Making the sound may include shaking the item, hitting the item, etc. The resulting sound or smell is compared to the sound/smell database 212 in order to determine the fine-grained identification.

Returning to decision box 314, if no fine-grained identification is necessary, then the method proceeds to box 318. In addition, once a fine-grained identification is performed in box 316, the method proceeds to box 318. At box 318, the processor 202 retrieves up one or more suitable actions from the actions database 214 for the operator to perform in order to properly recycle the item. The one or more actions can be presented to the operator via the speaker 114 or at the display 116, for example. The operator follows the actions in order to dispose of the item, as outlined in the actions stages 304, as detailed below.

In box 320, the action is presented to the operator. In box 322, the control unit 120 activates lights 112 and lids 105 based on the identified recycle category of the item. In box 324, the control unit 120 acknowledges receipt of the item in the appropriate bin or compliance of the object with a presented instruction.

In various embodiments, the operator is required to perform a plurality of actions. In this scenario, once the operator has performed an action as instructed and the control unit has acknowledged a corresponding compliance of the object (at box 324), the control unit returns to box 320 to present the next instruction to the operator. Thus, the flowchart can cycle through boxes 320, 322 and 324 as many times as necessary in order to have the operator complete the required actions.

In box 326, the control unit 120 analyzes the disposed recycled item by various parameters such as weight, sound and/or smell, in order to confirm that the object complies with the instructions as requested. In box 328, the control unit 120 notifies the operator of compliance. Such notification can be a congratulations or thank you, provided by speaker 114 or display 116 in order to reinforce the proper behavior by the operator. In box 330, the control unit 120 gathers statistics on a poor or non-complying object. In box 332, the control unit 120 revises the actions or adds an extra step to the action for the operator to perform in order to have the object comply with the requirement during subsequent recycling efforts. For example, if some operators frequently leave chips inside the bag of chips before disposing the bag, the system may create a new rule indicating that the operator should shake the bag of chips so the garbage collection station identifies if there is chips inside the bag so that the operator can be provided relevant instructions to empty the chips from the bag. Similarly a new rule should be created when, for example, operators start not emptying their bottles of soft drinks with the liquid inside before disposing in the garbage collection station.

Figure 4:
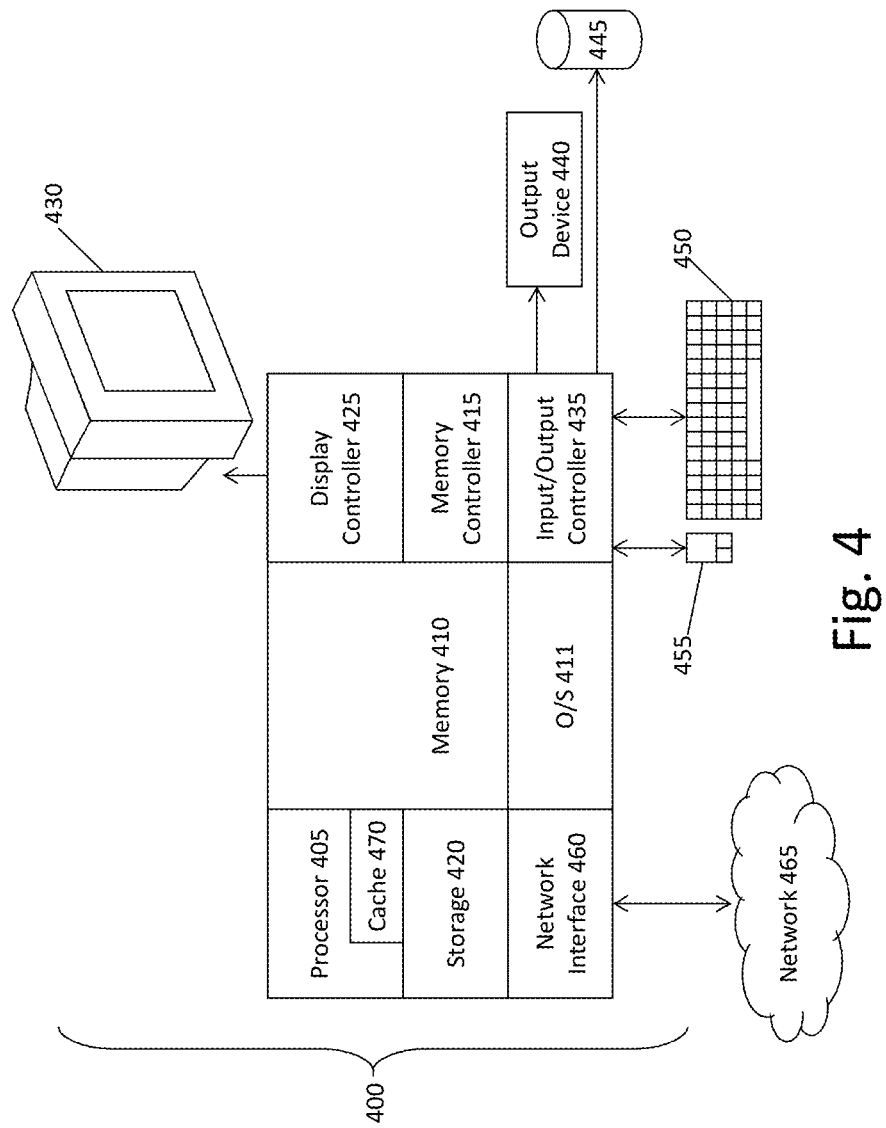
FIG. 4 illustrates a block diagram of a computer system for use in implementing a system or computer-implemented method according to embodiments of the invention.

FIG. 4 illustrates a block diagram of a computer system 400 for use in implementing a system or method according to some embodiments. The systems and methods described herein may be implemented in hardware, software (e.g., firmware), or a combination thereof. In some embodiments, the methods described may be implemented, at least in part, in hardware and may be part of the microprocessor of a special or general-purpose computer system 400, such as a personal computer, workstation, minicomputer, or mainframe computer.

In some embodiments, as shown in FIG. 4, the computer system 400 includes a processor 405, memory 410 coupled to a memory controller 415, and one or more input devices 445 and/or output devices 440, such as peripherals, that are communicatively coupled via a local I/O controller 435. These devices 440 and 445 may include, for example, a printer, a scanner, a microphone, and the like. Input devices such as a conventional keyboard 450 and mouse 455 may be coupled to the I/O controller 435. The I/O controller 435 may be, for example, one or more buses or other wired or wireless connections, as are known in the art. The I/O controller 435 may have additional elements, which are omitted for simplicity, such as controllers, buffers (caches), drivers, repeaters, and receivers, to enable communications.

The I/O devices 440, 445 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 405 is a hardware device for executing hardware instructions or software, particularly those stored in memory 410. The processor 405 may be a custom made or commercially available processor, a central processing unit (CPU), an auxiliary processor among several processors associated with the computer system 400, a semiconductor based microprocessor (in the form of a microchip or chip set), a macroprocessor, or other device for executing instructions. The processor 405 includes a cache 470, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 470 may be organized as a hierarchy of more cache levels (L1, L2, etc.).

The memory 410 may include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 410 may incorporate electronic, magnetic, optical, or other types of storage media. Note that the memory 410 may have a distributed architecture, where various components are situated remote from one another but may be accessed by the processor 405.

The instructions in memory 410 may include one or more separate programs, each of which comprises an ordered listing of executable instructions for implementing logical functions. In the example of FIG. 4, the instructions in the memory 410 include a suitable operating system (OS) 411. The operating system 411 essentially may control the execution of other computer programs and provides scheduling, input-output control, file and data management, memory management, and communication control and related services.

Additional data, including, for example, instructions for the processor 405 or other retrievable information, may be stored in storage 420, which may be a storage device such as a hard disk drive or solid state drive. The stored instructions in memory 410 or in storage 420 may include those enabling the processor to execute one or more aspects of the systems and methods of this disclosure.

The computer system 400 may further include a display controller 425 coupled to a display 430. In some embodiments, the computer system 400 may further include a network interface 460 for coupling to a network 465. The network 465 may be an IP-based network for communication between the computer system 400 and an external server, client and the like via a broadband connection. The network 465 transmits and receives data between the computer system 400 and external systems. In some embodiments, the network 465 may be a managed IP network administered by a service provider. The network 465 may be implemented in a wireless fashion, e.g., using wireless protocols and technologies, such as WiFi, WiMax, etc. The network 465 may also be a packet-switched network such as a local area network, wide area network, metropolitan area network, the Internet, or other similar type of network environment. The network 465 may be a fixed wireless network, a wireless local area network (LAN), a wireless wide area network (WAN) a personal area network (PAN), a virtual private network (VPN), intranet or other suitable network system and may include equipment for receiving and transmitting signals.

Systems and methods according to this disclosure may be embodied, in whole or in part, in computer program products or in computer systems 400, such as that illustrated in FIG. 4.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Many of the functional units described in this specification have been labeled as modules. Embodiments of the invention apply to a wide variety of module implementations. For example, a module can be implemented as a hardware circuit including custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like. Modules can also be implemented in software for execution by various types of processors. An identified module of executable code can, for instance, include one or more physical or logical blocks of computer instructions which can, for instance, be organized as an object, procedure, or function. Nevertheless, the executables of an identified module need not be physically located together, but can include disparate instructions stored in different locations which, when joined logically together, include the module and achieve the stated purpose for the module.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method of executing an interactive advisor, the computer-implemented method comprising:
   sensing an object to be recycled using a sensor;
   identifying a recyclable state of the object and providing an instruction to the operator to facilitate disposing the object based on the recyclable state, wherein the object includes two or more components having separate recycle categories and the instruction includes instructions for the operator to separate the object into its components and depositing each component into their respective recycle bins;
   opening, by the processor, the recycle bins suitable for the recycle categories; and
   instructing, by the processor, an operator to deposit the components of the object in the respective opened recycle bins.

2. The computer-implemented method of claim 1, wherein the recyclable state includes the object having garbage therein and the instruction includes separating the garbage from the object prior to depositing the object in the recycle bin.

3. The computer-implemented method of claim 1 further comprising determining a coarse-grain identification of the object using a visual sensor.

4. The computer-implemented method of claim 3 further comprising determining a fine-grain identification of the object using at least one of: a smell sensor; and an audio sensor.

5. The computer-implemented method of claim 1, further comprising determining the level of compliance of the object via measuring a parameter selected from: (i) weight; (ii) sound; and (iii) smell.

6. An interactive advisor, comprising:
   a sensor configured to obtain data related to an object; and
   a processor configured to:
      classify the object based on the data to identify a recycle category for the object;
      identify a recyclable state of the object and providing an instruction to the operator to facilitate disposing the object based on the recyclable state, wherein the object includes two or more components having separate recycle categories and the instruction includes instructions for the operator to separate the object into its components and depositing each component into their respective recycle bins;
      open the recycle bins for the identified recycle categories; and
      instruct the operator to deposit the components of the object in the respective opened recycle bins.

7. The interactive advisor of claim 6, wherein the recyclable state includes the object having garbage therein and the instruction includes separating the garbage from the object prior to depositing the object in the recycle bin.

8. The interactive advisor of claim 6, wherein the processor is further configured to determine a coarse-grain identification of the object using data obtained at a visual sensor.

9. The interactive advisor of claim 8, wherein the processor is further configured to determine a fine-grain identification of the object using data obtained by at least one of: a smell sensor; and an audio sensor.

10. The interactive advisor of claim 6, wherein the processor is further configured to determine the level of compliance of the object via measuring a parameter selected from: (i) weight; (ii) sound; and (iii) smell.

11. A computer program product for operating a garbage collection station, the computer program product comprising a computer readable storage medium having program instructions embodied therewith, the program instructions executable by a processor to cause the processor to perform operations comprising:
   sensing an object to be recycled using a sensor;
   identifying a recyclable state of the object and providing an instruction to the operator to facilitate disposing the object based on the recyclable state, wherein the object includes two or more components having separate recycle categories and the instruction includes instructions for the operator to separate the object into its components and depositing each component into their respective recycle bins
   opening the recycle bins suitable for the recycle categories; and
   instructing an operator to deposit the components of the object in the respective opened recycle bins.

12. The computer program product of claim 11, wherein the recyclable state includes the object having garbage therein and the instruction includes separating the garbage from the object prior to depositing the object in the recycle bin.

13. The computer program product of claim 11, wherein the operations further comprise determining a coarse-grain identification of the object using a visual sensor, and determining a fine-grain identification of the object using at least one of: a smell sensor; and an audio sensor.

14. The computer program product of claim 11, wherein the operations further comprise determining the level of compliance of the object via measuring a parameter selected from: (i) weight; (ii) sound; and (iii) smell.

* * * * *